(12) United States Patent
Williamson et al.

(10) Patent No.: US 7,439,537 B2
(45) Date of Patent: Oct. 21, 2008

(54) DIVINYLFLUORENES

(75) Inventors: Alexander Williamson, Mortsel (BE); Paul Callant, Edegem (BE)

(73) Assignee: Agfa Graphics, N.V., Mortsel (BE)

( * ) Notice: Subject to any disclaimer, the term of this patent is extended or adjusted under 35 U.S.C. 154(b) by 0 days.

(21) Appl. No.: 11/193,850

(22) Filed: Jul. 29, 2005

(65) Prior Publication Data

US 2006/0022193 A1 Feb. 2, 2006

Related U.S. Application Data

(60) Provisional application No. 60/602,106, filed on Aug. 17, 2004.

(30) Foreign Application Priority Data

Jul. 30, 2004 (EP) .................................. 04103671

(51) Int. Cl.
H01L 29/08 (2006.01)
G03C 1/73 (2006.01)
C07C 43/20 (2006.01)

(52) U.S. Cl. ...................... 257/40; 430/270.1; 568/633
(58) Field of Classification Search .............. 430/270.1; 257/40; 568/633
See application file for complete search history.

(56) References Cited

U.S. PATENT DOCUMENTS

| | | |
|---|---|---|
| 3,784,557 A | 1/1974 | Cescon |
| 3,980,713 A | 9/1976 | Matsunaga et al. |
| 4,062,686 A | 12/1977 | Van Allan et al. |
| 4,119,466 A | 10/1978 | Van Allan et al. |
| 4,250,248 A | 2/1981 | Faust |
| 4,274,062 A | 6/1981 | Brinkmann et al. |
| 4,410,621 A | 10/1983 | Wada et al. |
| 4,459,349 A | 7/1984 | Tanaka et al. |
| 4,555,474 A | 11/1985 | Kawamura et al. |
| 4,987,053 A | 1/1991 | Gersdorf et al. |
| 5,489,499 A | 2/1996 | Yumoto |
| 5,879,837 A | 3/1999 | Yoshinaga |
| 6,197,472 B1 | 3/2001 | Konrad et al. |
| 6,344,286 B1 | 2/2002 | Kim et al. |
| 6,576,396 B1 | 6/2003 | Leichsenring et al. |
| 7,241,557 B2 * | 7/2007 | Williamson et al. ...... 430/284.1 |
| 2003/0091859 A1 | 5/2003 | Cho et al. |
| 2006/0024614 A1 * | 2/2006 | Williamson .............. 430/270.1 |

FOREIGN PATENT DOCUMENTS

| | | |
|---|---|---|
| DE | 14 70 154 A1 | 1/1972 |
| DE | 20 64 079 A1 | 7/1972 |
| DE | 28 22 190 A1 | 11/1979 |
| DE | 32 11 312 A1 | 10/1982 |
| EP | 0 24 629 A2 | 3/1981 |
| EP | 0 107 792 A1 | 5/1984 |
| EP | 0 215 453 A2 | 3/1987 |
| EP | 0 287 818 A2 | 10/1988 |
| EP | 0 316 706 A2 | 5/1989 |
| EP | 0 352 630 B1 | 8/1994 |
| EP | 0 624 580 A1 | 11/1994 |
| EP | 0 091 247 A2 | 4/2001 |
| GB | 2 313 127 A | 11/1997 |
| JP | 07 196 632 | 8/1995 |
| JP | 10 152 678 A2 | 9/1998 |

OTHER PUBLICATIONS

European Search Report 04 10 3671 (Jan. 4, 2005).
Kauffman et al.; *Journal of Organic Chemistry*; 68(3); pp. 839-853 (2003).
*Makromolekulare Chemie*; 176(3); pp. 539-559 (1975).
Mongin et al.; *Tetrahedron Letters*; 44(44); pp. 8121-8125 (2003).
Patra et al.; *Chemistry of Materials*; 14(10); pp. 4044-4048 (2002).

* cited by examiner

*Primary Examiner*—Golam M. M. Shameem
*Assistant Examiner*—Joseph R Kosack
(74) *Attorney, Agent, or Firm*—Leydig, Voit & Mayer, Ltd.

(57) ABSTRACT

New divinylfluorene compounds according to one of formulae (II) or (III):

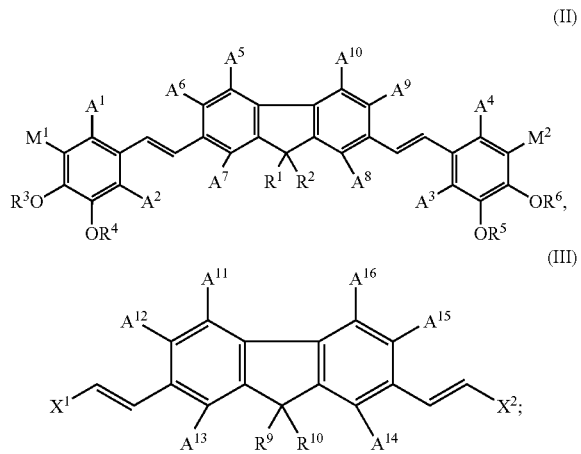

a new synthetic route to divinylfluorene compounds; and the use of the new compounds as sensitizers, optical brighteners and electroluminescent materials.

6 Claims, No Drawings

DIVINYLFLUORENES

CROSS-REFERENCE TO RELATED PATENT APPLICATIONS

This application claims the benefit of U.S. Provisional Application No. 60/602,106 filed Aug. 17, 2004, which is incorporated by reference. In addition, this application claims the benefit of European Application No. 04103671.6 filed Jul. 30, 2004, which is also incorporated by reference.

FIELD OF THE INVENTION

The present invention relates to new classes of divinylfluorene compounds, a new synthetic approach for divinylfluorene compounds and the use of said new compounds as optical brighteners, optical sensitizers and for electroluminescent materials and devices.

BACKGROUND OF THE INVENTION

The fluorene ring system and its numbering is demonstrated with the following formula:

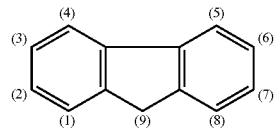

Commonly known divinylfluorene compounds belong to the following (2,7-distyryl) core structure (I):

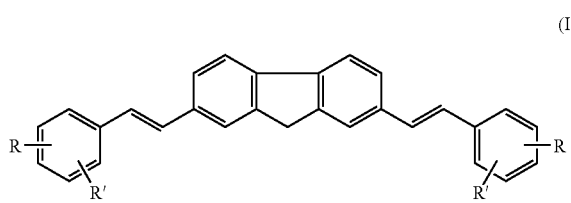

(I)

The unsubstituted compound of formula (I), wherein R and R' each represent a hydrogen atom and the disubstituted compounds, wherein both R and/or both R' represent a substituent selected from e.g. a hydroxy, alkoxy, dialkylamino, diarylamino or halogen group, are described in e.g. U.S. Pat. No. 3,980,713, US 2003/091859, GB 2 313 127 and U.S. Pat. No. 6,344,286.

For use as a luminescent material for organic and polymer-based electroluminescence elements, the distyryl fluorene compounds can also be polymerized or copolymerized as described e.g. in US 2003/091859.

Besides the aforementioned distyryl fluorene compounds (I) are also known the following di(vinyl hetaryl)fluorene compounds (F-1) and (F-2):

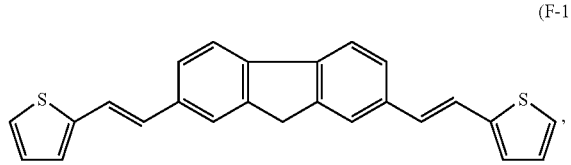

(F-1)

see e.g. Makromolekulare Chemie (1975), 176(3), 539-59, and

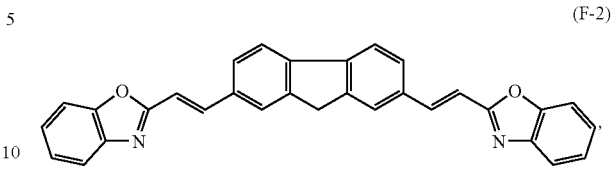

(F-2)

see e.g. JP 10 152 678 A2.

Apparently there is only known a very limited number of divinyl fluorene compounds from the prior art and such known compounds have drawbacks with respect to their properties when used as a) sensitizers for e.g. printing plate precursors, b) optical brighteners or c) monomers used for the preparation of electroluminescence elements.

When used as sensitizers for e.g. printing plate precursors, the sensitivity of the known compounds is still unsatisfactory and frequently there are observed so-called pinhole defects, that have an irregular crystal-like shape. Defects called pinholes are areas having lateral dimensions of about 50 to 500 μm on the processed printing plate, that don't take up ink and therefore result in exposed areas that don't print. This unfavorable effect is particularly noticeable, if the printing plate precursor is stored before exposure and processing thereof.

When used as optical brightener, there is a demand to have a broader range of substances to best fit the absorbance and emittance spectra as well as to increase the quantum efficiency. There is further a need to find optical brighteners that can easily be formulated and then incorporated in the material.

When used in polymeric form for electroluminescent elements, there still is a need for a broader range of compounds that allow the production of uniform films and that have an improved stability.

The synthesis of divinyl fluorene compounds is e.g. disclosed in U.S. Pat. No. 3,980,713. Said synthesis is carried out by a palladium catalyzed reaction of a vinyl benzene with a 2,7-dihalogenofluorene compound. This method is disadvantageous, as many vinyl aryl compounds like e.g. 3,4,5-trialkoxystyrene, 3,5-dialkoxy-4-hydroxystyrene or vinyl hetaryl compounds are not readily available. A similar method with the same restrictions is described in U.S. Pat. No. 6,344,286 and US 2003/091859.

From GB 2 313 127 is known a synthetic route to polymers comprising 2,7-distyrylfluorene monomers, wherein the polymers are formed by Wittig reaction of 2,7-bistriphenylphosphonium methylene-9,9-dialkylfluorene with dialdehydes. From the description is also known the synthesis of 2,7-dibromomethyl-9,9-dialkyl fluorenes by a) 9,9-dialkylation and b) 2,7-dibromomethylation of fluorene. The synthetic method is disadvantageous, as the product can not easily be purified.

From A. Patra et al., Chemistry of Materials (2002), 14(10), 4044-4048, is known a Wittig reaction on only one side of the fluorene unit using Diphenylaminobenzaldehyde.

According to J. M. Kauffman and G. Moyna, Journal of Organic Chemistry (2003), 68(3), 839-853, 2,7-bis-phosphonate esters of fluorene can be reacted with p-substituted aldehydes to yield 2,7-distyrylfluorenes. The disadvantage of this method is, that 5 reaction steps are necessary to obtain the 2,7-distyrylfluorenes from 9,9-dialkyl-2,7-dibromofluorene which itself must be prepared by alkylation of 2,7-dibromofluorene.

O. Mongin et al. describe in Tetrahedron Letters (2003), 44(44), 8121-8125, a synthetic method, wherein 9,9-dialkylfluorene is first converted to 2,7-dibromo-9,9-dialkylfluorene and then to 2,7-diformyl-9,9-dialkylfluorene. This is then reacted with [4-(dibutylamino)phenyl]methyltriphenylphosphonium bromide. The drawback is, that arylmethyltriphenylphosphonium salts are not readily available, relative to the analogous aldehydes.

From the foregoing discussion it becomes evident, that the known synthesis methods for divinylfluorene compounds are still unsatisfactory.

SUMMARY OF THE INVENTION

It is an object of the present invention, to find new divinylfluorene compounds, that are suitable as e.g. optical brighteners, sensitizers for light sensitive materials or precursors for electroluminescent materials, that do not show the drawbacks as discussed above.

It is also an object of the present invention to find a synthesis for divinylfluorene compounds, that does not use many reaction steps, that yields very pure products without the necessity of difficult purifying steps and that only uses readily available reagents.

Further objects of the present invention are the use of the divinylfluorene compounds of the present invention as sensitizers for light sensitive materials, as optical brighteners and as monomers for the synthesis of polymeric light emitting materials of electroluminescent elements.

Preferred embodiments of the present invention are defined in the dependent claims.

DETAILED DESCRIPTION OF THE INVENTION

The objects of the present invention are achieved by divinylfluorene compounds according to one of formulae (II) or (III):

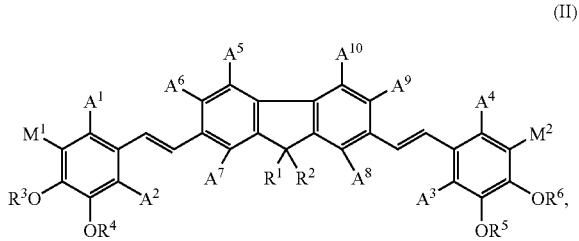

(II)

wherein
$A^1$ to $A^{10}$ mutually independent mean a substituent selected from a non-metallic atom group,
$M^1$ means a hydrogen atom or $OR^7$,
$M^2$ means a hydrogen atom or $OR^8$,
$R^1$, $R^2$ mutually independent mean a substituent selected from a non-metallic atom group, and
$R^3$ to $R^8$ mutually independent mean a hydrogen atom, alkyl, an alkyl chain containing double or triple bonds, alkenyl, alkynyl, or any non-metallic atom group linked to the oxygen by a carbon atom, and wherein one or more pairs of said substituents can jointly mean the remaining atoms to form a ring; or

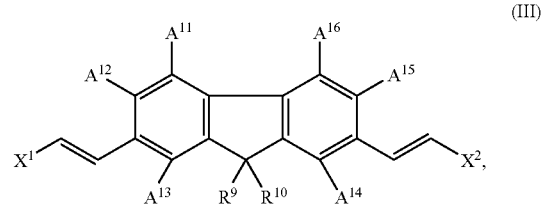

(III)

wherein
$A^{11}$ to $A^{16}$ mutually independent mean a substituent selected from a non-metallic atom group,
$R^9$, $R^{10}$ mutually independent mean a substituent selected from a non-metallic atom group,
$X^1$, $X^2$ mutually independent mean a group of formula (IV)

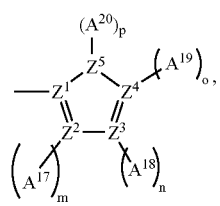

(IV)

wherein $Z^1$ to $Z^5$ mutually independently mean non-hydrogen, non-metallic atoms,
$A^{17}$ to $A^{20}$ mutually independent mean a substituent selected from a non-metallic atom group,
m, n, o mutually independent mean 0 or 1 and
p means 0, 1 or 2;

and wherein one or more pairs of the substituents in formulae (II), (III) and/or (IV) can jointly mean the remaining atoms to form a ring;

with the proviso that if $R^9$, $R^{10}$ and $A^{11}$ to $A^{16}$ all mean a hydrogen atom, then $X^1$ and $X^2$ do not both mean an unsubstituted 2-thienyl group and do not both mean an unsubstituted 2-benzoxazolyl-group.

The values of m,n,o and p are determined by the possible valencies of the atoms $Z^1$ to $Z^5$. The values of m, n and o calculate as possible valency of $Z^2$, $Z^3$ or $Z^4$ respectively minus 3 and the value of p calculates as possible valency of $Z^5$ minus 2. A possible valency is defined in the context of the present invention as the valency or the valencies an atom $Z^1$ to $Z^5$ can have in a ring of formula (IV). Examples of possible valencies are 4 for a carbon atom, 3 for an uncharged and 4 for a positively charged nitrogen atom, 2 for an oxygen atom and 2 for a sulfur atom.

Preferably $Z^1$ to $Z^4$ mutually independent mean an unsubstituted nitrogen atom, or a carbon atom that is substituted by a substituent selected from a non-metallic atom group,
$Z^5$-$(A^{20})_p$ means O, S, $CH_2$, $CHR^{11}$, $CR^{12}R^{13}$ or $NR^{14}$ and
$R^{11}$ to $R^{14}$ mutually independent mean a substituent selected from a non-metallic atom group.

The non-metallic atom group according to the present invention preferably consists of a hydrogen atom or alkyl, alkenyl, alkynyl, aryl, heterocyclyl, hydroxy, carboxy, carbalkoxy, halogeno, alkoxy, aryloxy, heterocyclyloxy, alkylthio, arylthio, heterocyclylthio, alkylseleno, arylseleno, heterocyclylseleno, acyl, acyloxy, alkylsulfonyl, aminosulfonyl, acylamino, cyano, nitro, amino or mercapto groups, wherein heterocycle means a saturated, unsaturated or aromatic heterocycle and acyl means the remaining residue of an aliphatic, olefinic or aromatic carbon, carbaminic, sulfonic, amidosulfonic or phosphonic acid.

In a preferred embodiment of the present invention the non-metallic atom group consists of a hydrogen atom or alkyl, alkenyl, aryl, heterocyclyl, hydroxy, carboxy, carbalkoxy, halogeno, alkoxy, aryloxy, heterocyclyloxy, alkylthio, arylthio, heterocyclylthio, acyl, acyloxy, acylamino, cyano, nitro, amino, or mercapto groups, wherein heterocycle has the same meaning as given above and acyl means the remaining residue of an aliphatic, olefinic or aromatic carbon, sulfonic, amidosulfonic or phosphonic acid.

Alkyl, alkylene, alkenyl, alkenylene, alkynyl and alkynylene groups according to the present invention can be linear (straight chain), branched or cyclic.

The alkyl, alkylene, alkenyl, alkenylene, alkynyl, alkynylene, aryl, heterocyclyl, alkoxy and alkylthio groups of the present invention can be optionally substituted by a substituent selected from the non-metallic atom group of the present invention and the substituents can be selected to adjust the solubility of the divinylfluorene compound and preferably may be halogeno, alkoxy, alkylthio, carbalkoxy, acyloxy or hydroxy.

Said one or more pairs of substituents that jointly can mean the remaining atoms to form a ring preferably are selected from $A^1$ with $R^3$; $R^3$ with $R^4$; $R^4$ with $R^5$; $R^5$ with $A^2$; $A^7$ with $R^1$ or $R^2$; $R^1$ with $R^2$; $A^8$ with $R^1$ or $R^2$; $A^3$ with $R^6$; $R^6$ with $R^7$; $R^7$ with $R^8$; $R^8$ with $A^4$; $A^9$ with $A^{10}$; $A^5$ with $A^6$; $A^{13}$ with $R^9$ or $R^{10}$; $R^9$ with $R^{10}$; $A^{14}$ with $R^9$ or $R^{10}$; $A^{15}$ with $A^{16}$; $A^{11}$ with $A^{12}$; $A^{17}$ with $A^{18}$; $A^{18}$ with $A^{19}$; and $A^{19}$ with $A^{20}$.

In a particular preferred embodiment of the present invention, said one or more pairs of substituents that jointly can mean the remaining atoms to form a ring are selected from $R^3$ with $R^4$; $R^4$ with $R^5$; $R^1$ with $R^2$; $R^6$ with $R^7$; $R^7$ with $R^8$; $R^9$ with $R^{10}$; $A^{17}$ with $A^{18}$; $A^{18}$ with $A^{19}$; and $A^{19}$ with $A^{20}$.

A ring according to the present invention means a carbo- or heterocyle, that can be substituted by substituents selected from e.g. the non-metallic atom group of the present invention, that can be saturated, unsaturated or aromatic and that itself can be substituted by further rings. Preferably the ring is a 5 to 8 membered ring, and in particular a 5 or 6 membered ring.

In a further preferred embodiment of the present invention the divinylfluorene compound has a structure according to formula (II), wherein at least one of the substituents $R^1$ to $R^8$ is different from a hydrogen atom or of formula (III), wherein at least one of the substituents $R^9$ or $R^{10}$ is different from a hydrogen atom.

In another preferred embodiment of the present invention the divinylfluorene compound has a structure according to one of formulae (II) or (III), wherein $A^1$ to $A^{16}$ mean hydrogen and/or $R^3$ to $R^8$ mutually independent mean a substituent selected from hydrogen or alkyl and/or $R^1$, $R^2$, $R^9$, $R^{10}$ mutually independent mean straight chain or branched alkyl preferably having 1 to 20 carbon atoms and particularly preferred having 1 to 10 carbon atoms.

If the divinylfluorene compound of the present invention is used as a sensitizer, further advantages with respect to the sensitivity can be achieved with compounds of the following general formula (III-A):

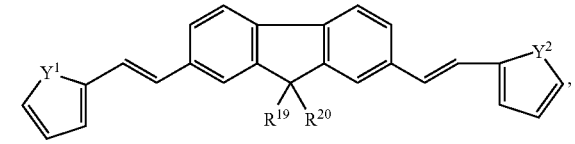

(III-A)

wherein $Y^1$, $Y^2$ mutually independent mean O, S, NH or N-alkyl and $R^{19}$, $R^{20}$ mutually independent mean an unsubstituted linear or branched alkyl group having 1 to 20 carbon atoms and preferably having 1 to 10 carbon atoms, and wherein the hetero rings comprising $Y^1$ and $Y^2$ are mutually independent each substituted by three members selected from a non-metallic atom group. Preferably the hetero rings are each substituted by at least one hydrogen atom, in particular by at least two hydrogen atoms and further preferred by three hydrogen atoms.

When used as sensitizers, further advantages with respect to the sensitivity can be achieved with symmetrical divinylfluorenes. A symmetrical divinylfluorene compound according to the present invention means a compound of formula (II), wherein $A^1=A^4$, $A^2=A^3$, $R^3=R^8$, $R^4=R^7$, $R^5=R^6$, $A^5=A^{10}$, $A^6=A^9$, $A^7=A^8$ and $R^1=R^2$; or a compound of formula (III), wherein $A^{11}=A^{16}$, $A^{12}=A^{15}$, $A^{13}=A^{14}$, $R^9=R^{10}$ and $X^1=X^2$.

Divinylfluorene compounds of structure (II) are preferred over those of structure (III).

The following structures are examples of preferred divinylfluorene compounds of the present invention:

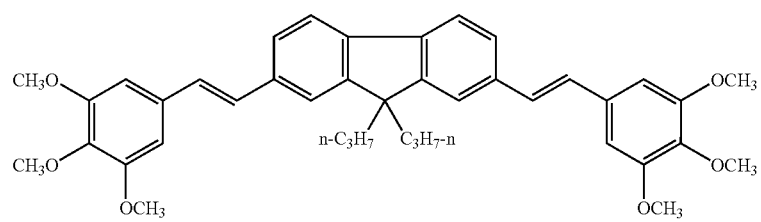

(II-1)

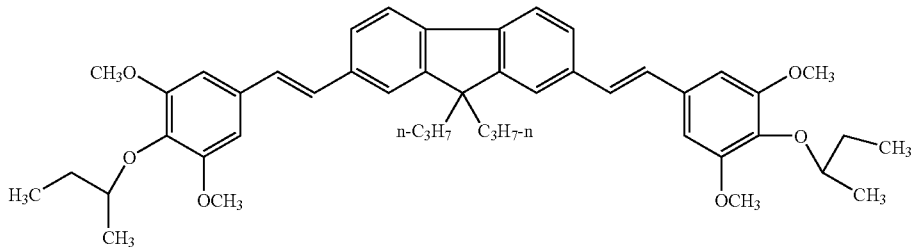
(II-2)
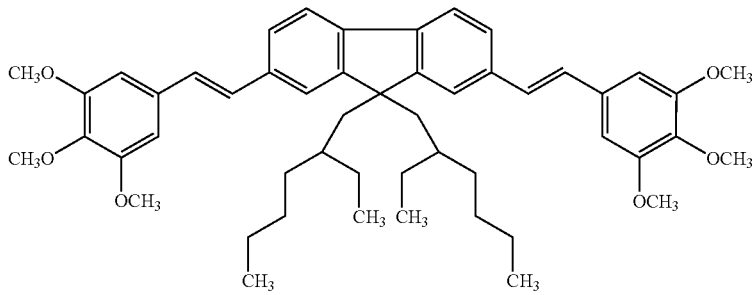
(II-3)
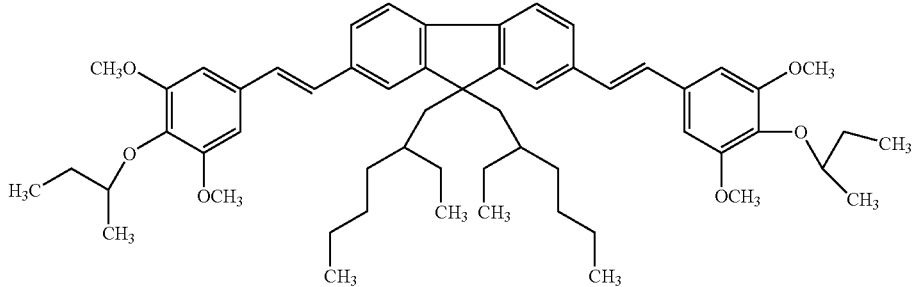
(II-4)
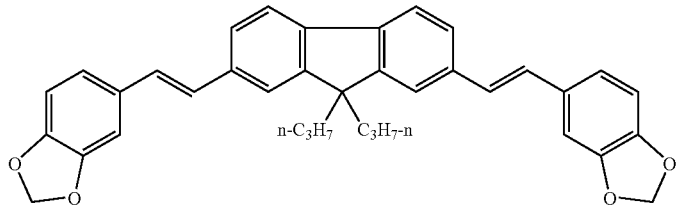
(II-5)
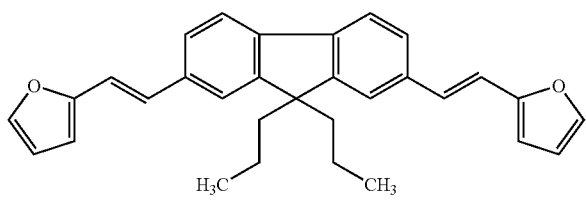
(III-1)
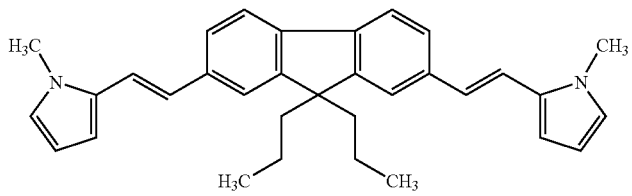
(III-2)

The divinylfluorene compound of the present invention can be used as a single compound or as a mixture of compounds of formulae (II) and/or (III). The overall amount of these compounds ranges from 0.1 to 10% by weight, preferably 0.5 to 8% by weight with respect to the total weight of the non-volatile compounds in the composition. The divinylfluorene compound of the present invention can also be combined with known divinylfluorenes and/or with known compounds having the same function, e.g. known sensitizers, optical brighteners or electroluminescent materials.

The divinylfluorene compounds useful for the present invention, in particular when used as sensitizers, preferably have a good solubility in common solvents. It has been found, that compounds having a solubility of 0.5 g, in particular 1.5 g sensitzer per 100 mL methylethylketone or more are particularly advantageous as sensitizers with respect to pinhole defects as well as sensitivity.

The compounds of formulae (II) and/or (III) are preferably used as sensitizers in composition that are photopolymerizable upon absorption of light in the wavelength range from 350 to 430 nm, preferably from 380 to 430 nm and in particular from 390 to 420 nm.

The divinylfluorene compounds of the present invention can be synthesized by known methods as disclosed above, but preferably they are synthesized by a new synthetic route that surprisingly has been found and that allows to synthesize a broad range of divinyl fluorene compounds by only four steps that all give high yields and only require readily available reactants.

This new synthetic method of the present invention is characterized in that in the first step the 9-position of a 2,7,9-unsubstituted fluorene compound (substituted by hydrogen atoms at positions 2, 7 and 9) is dialkylated using a strong base and an alkyl halide, in step 2 the 9,9-dialkylated fluorene is 2,7-bis-halomethylated, this intermediate is then reacted in step 3 with trialkylphosphite to 2,7-bis(dialkylphosphonatomethyl)-9,9-dialkylfluorene, which gives in step 4 on reaction with an aromatic aldehyde 2,7-divinylfluorene compounds, in particular those of formulae (II) and (III), in high yield.

Step 1 preferably is done in polar aprotic solvents like dimethylformamide (DMF), dimethylsulfoxide (DMSO) or an ether like tetrahydrofurane (THF). The fluorene is first deprotonated, in particular using strong bases like sodium hydride, n-butyl lithium (LiButyl-n) or tert-butyl lithium (LiButyl-t), and then the alkyl halide, preferably a primary or secondary alkyl bromide or chloride is carfully added.

Step 2 preferably is done with paraformaldehyde and hydrobromic acid.

Step 4 is preferably done with a base such as sodium hydride (NaH), sodium ethoxylate (NaOEthyl), sodium methoxylate (NaOMethyl), lithium ethoxylate (LiOEthyl), lithium methoxylate (LiOMethyl), potassium tert-butyloxylate (KOButyl-t), sodium tert-butyloxylate (NaOButyl-t), lithium hydroxide (LiOH), potassium hydroxide (KOH), di-sodium carbonate ($Na_2CO_3$) or di-potassium carbonate ($K_2CO_3$) in a polar solvent such as DMF, ethanol, DMSO, sulpholane or an ether like THF.

The following example synthesis of compounds (II-1), (II-2) and (II-5) are good starting points for the conditions and reagents useful for the synthetic method of the present invention, but the present invention is not restricted to this example. On the contrary a person skilled in the art can easily adapt the conditions such as reaction temperatures and times as well as the solvents and can use known functionally equivalent reagents to yield with only 4 steps a wide variety of divinylfluorenes as very pure products without the necessity of difficult purifying steps and only using readily available reagents.

EXAMPLE SYNTHESIS OF DIVINYLFLUORENE (II-1)

Step 1: 9,9-Dipropylfluorene (2)

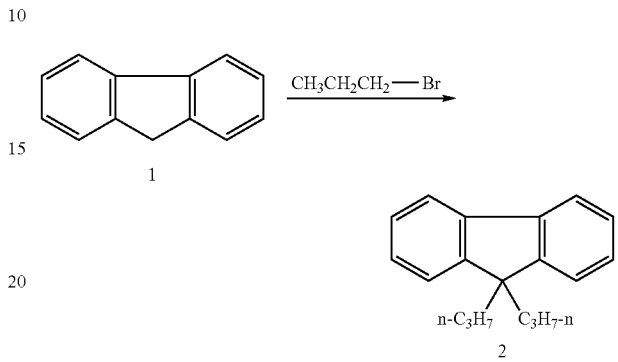

To a solution of fluorene (1) (41.5 g) in dimethylformamide (300 mL) at 20° C. was added sodium hydride (24.7 g) in portions. The red solution was stirred for 2 hours at 35° C. until no more gas was evolved. To this solution was added 1-bromopropane (62.7 g) drop-wise over 1 hour at 5° C. and then the mixture was stirred for 1 hour at 40° C.

The suspension was poured into ice-water (1.5L) and the resultant oil was dissolved in methylene chloride (0.5L). The organic phase was washed with water, dried over magnesium sulfate and the solvent was removed under reduced pressure. The residue was purified by vacuum distillation (122-125° C./0.5 mmHg). After cooling, 2 was obtained as a crystalline product (47.0 g, 74%).

Step 2: 2,7-Bis(bromomethyl)-9,9-dipropylfluorene (3)

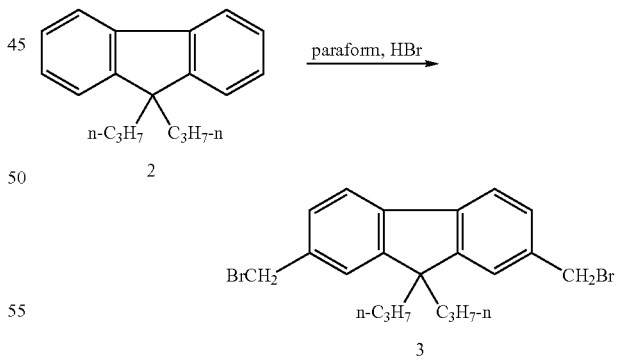

To a solution of 9,9-dipropylfluorene 2 (25.0 g) in acetic acid (50 mL) was added paraformaldehyde (paraform) (18.0 g) at 15° C. To the mixture was then added a solution of hydrogen bromide in acetic acid (250 mL, 30% w/w) over 0.5 hours, and the solution was stirred at 60° C. for 5 hours. The reaction mixture was poured into ice-water (1.0L) and stirred for 0.5 hours. The precipitate was filtered off and purified by stirring in acetonitrile (200 mL) at 40° C., filtering and drying to give 3 as a yellow powder (33.0 g, 77%).

Step 3: 2,7-Bis(diethylphosphonatomethyl)-9,9-dipropylfluorene (4)

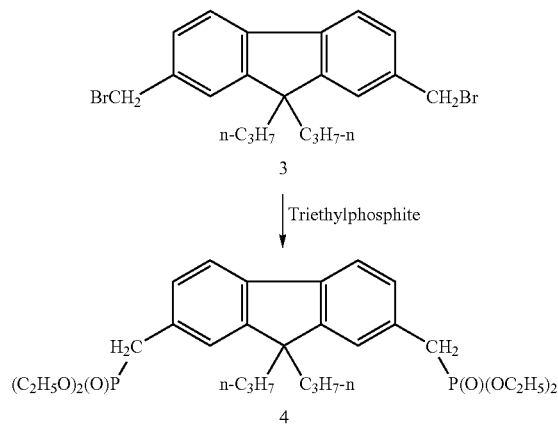

A mixture of 2,7-Bis(bromomethyl)-9,9-dipropylfluorene (3) (33.0 g) and triethylphosphite (40 mL) was stirred for 3 hours at 150° C. Excess triethylphosphite was removed at reduced pressure at 100° C. and the resultant oil crystallised from hexane. After drying, 4 was obtained as a white powder (31.5 g, 67.5%).

Step 4: divinylfluorene (II-1)

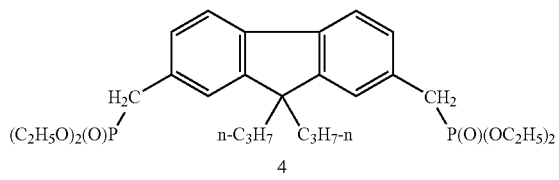

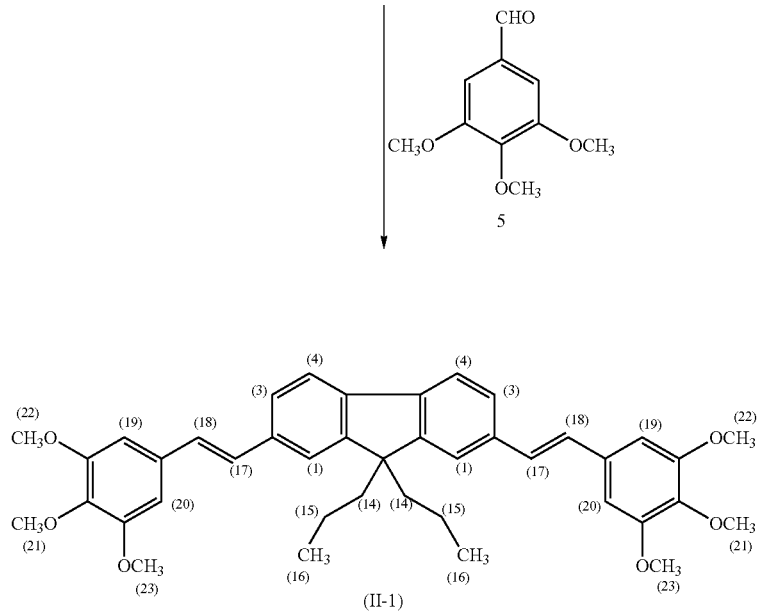

A suspension of 2,7-Bis(diethylphosphonatomethyl)-9,9-dipropylfluorene (4) (2.15 g, 4.0 mmol), 3,4,5-trimethoxybenzaldehyde (5) (1.76 g, 9.0 mmol), and potassium hydroxide (0.75 g, 13 mmol) in THF (20 mL) and DMSO (1 mL) was heated at 70° C. for 4 hours. The suspension was diluted with Ethanol (50 mL) and the solvent removed under vacuum. The product was purified by refluxing in Methanol followed by filtration. After drying, (II-1) was obtained as a pale yellow powder (1.90 g, 76%). The UV/VIS spectrum of (II-1) in methyl ethyl ketone (MEK) has two maxima at 380 nm and at 399 nm with a molar extinction coefficient of 89724 Mol$^{-1}$ cm$^{-1}$ and 72301 Mol$^{-1}$ cm$^{-1}$ respectively. Under UV irradiation in MEK, (II-1) shows a strong blue fluorescence with fluorescence peaks at 417 nm and 439 nm. The fluorescence quantum yield of (II-1) relative to the anthracene standard is 0.65 (in MEK solvent, not degassed). The $^1$H-NMR data in CDCl$_3$ are summarized in table 1; in the table s means singlet, d means doublet, dd means double doublet, m means multiplet and J means the coupling constant.

TABLE 1

| $^1$H-NMR data of (II-1) | | |
|---|---|---|
| Hydrogen position | Chemical shift/ ppm | Coupling (Coupling constant) |
| (3) | 7.49 | dd (J = 8 Hz, 2 Hz) |
| (4) | 7.67 | d (J = 8 Hz) |
| (1) | 7.48 | d (J = 2 Hz) |
| (14) | 2.01 | m |
| (15) | 0.71 | m |

TABLE 1-continued

<sup>1</sup>H-NMR data of (II-1)

| Hydrogen position | Chemical shift/ ppm | Coupling (Coupling constant) |
|---|---|---|
| (16) | 0.71 | m |
| (17) | 7.10 | d (J = 16 Hz) |
| (18) | 7.10 | d (J = 16 Hz) |
| (19), (20) | 6.79 | s |
| (21) | 3.89 | s |
| (22), (23) | 3.93 | s |

EXAMPLE SYNTHESIS OF DIVINYLFLUORENE (II-2)

Steps 1 to 3 were run in the same way as described for the synthesis of (II-1).

Step 4: divinylfluorene (II-2)

strong blue fluorescence with fluorescence peaks at 419 nm and 444 nm. The fluorescence quantum yield of (II-2) relative to the anthracene standard is 0.66 (in MEK solvent, not degassed). The $^1$H-NMR data in CDCl$_3$ are summarized in table 2.

TABLE 2

$^1$H-NMR data of (II-2)

| Hydrogen position | Chemical shift/ ppm | Coupling (Coupling constant) |
|---|---|---|
| (3) | 7.49 | dd (J = 8 Hz, 2 Hz) |
| (4) | 7.65 | d (J = 8 Hz) |
| (1) | 7.48 | d (J = 2 Hz) |
| (14) | 2.01 | m |
| (15) | 0.71 | m |
| (16) | 0.71 | m |
| (17) | 7.10 | d (J = 16 Hz) |
| (18) | 7.10 | d (J = 16 Hz) |
| (19), (20) | 6.79 | s |
| (21) | 4.20 | m |
| (22), (23) | 3.90 | s |

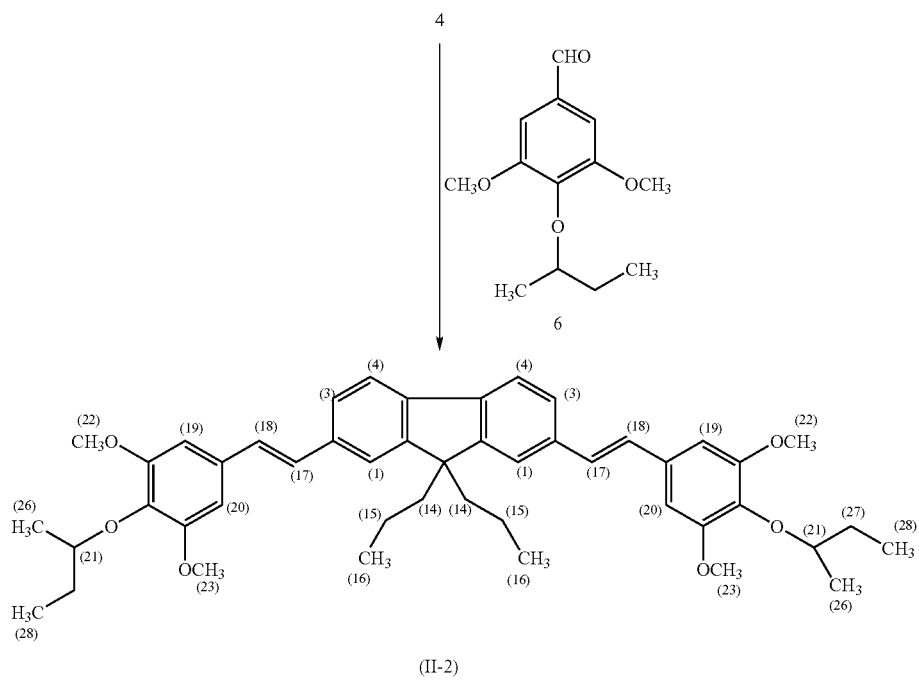

To a solution of 2,7-Bis(diethylphosphonatomethyl)-9,9-dipropylfluorene (4) (26.8 g) and 3,5-dimethoxy-4-(1-methylpropoxy)-benzaldehyde (6) (26.2 g) in tetrahydrofuran (200 mL) was added potassium hydroxide (8.4 g) and dimethylsulfoxide (5.0 mL). The suspension was stirred at 70° C. for 4 hours and then isopropanol (150 mL) was added. The solvent of the supernatant solution was removed at reduced pressure and the resultant oil was stirred in methanol (200 mL). The precipitate was filtered off and purified by stirring in boiling ethanol (200 mL) two times. After drying, (II-2) was obtained as a pale yellow powder (25.8 g, 72%). The UV/VIS spectrum of (II-2) in methyl ethyl ketone (MEK) has two maxima at 382 nm and at 402 nm with a molar extinction coefficient of 93092 Mol$^{-1}$ cm$^{-1}$ and 75139 Mol$^{-1}$ cm$^{-1}$ respectively. Under UV irradiation in MEK, (II-2) shows a TABLE 2-continued $^1$H-NMR data of (II-2)

| Hydrogen position | Chemical shift/ ppm | Coupling (Coupling constant) |
|---|---|---|
| (26) | 1.25 | d (J = 6 Hz) |
| (27) | 1.80, 1.61 | m |
| (28) | 1.00 | t (J = 7 Hz) |

EXAMPLE SYNTHESIS OF DIVINYLFLUORENE (II-5)

Steps 1 to 3 were run in the same way as described for the synthesis of (II-1).

Step 4: divinylfluorene (II-5)

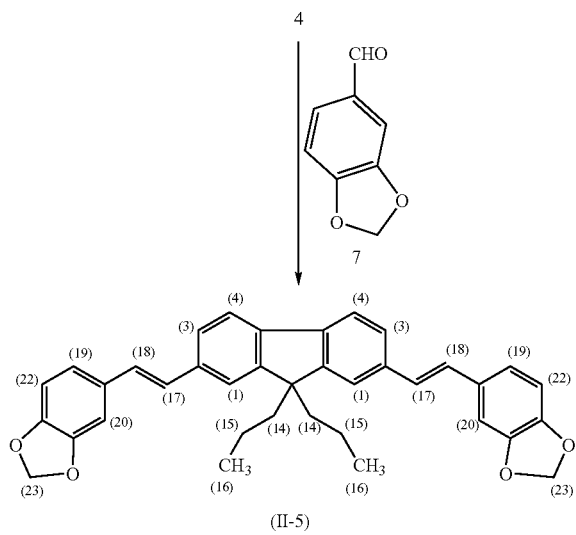

A suspension of 2,7-bis(diethylphosphonatomethyl)-9,9-dipropylfluorene (4) (2.70 g, 5 mmol), 3,4-methylenedioxy-benzaldehyde (7) (1.60 g, 11 mmol) and potassium hydroxide (0.85 g, 15 mmol) in THF (30 mL) and DMSO (1 mL) was heated at 70° C. for 7 hours. The suspension was diluted with Ethanol (50 mL) and the solvent removed under vacuum. The product was purified by refluxing in Methanol followed by filtration. After drying, (II-5) was obtained as a pale yellow powder (1.95 g, 72%). The UV/VIS spectrum of (II-5) in methyl ethyl ketone (MEK) has two maxima at 382 nm and at 401 nm with a molar extinction coefficient of 79099 Mol$^{-1}$ cm$^{-1}$ and 63911 Mol$^{-1}$ cm$^{-1}$ respectively. Under UV irradiation (II-5) shows a strong blue fluorescence. The $^1$H-NMR data in CDCl$_3$ are summarized in table 3.

TABLE 3

$^1$H-NMR data of (II-5)

| Hydrogen position | Chemical shift/ ppm | Coupling (Coupling constant) |
|---|---|---|
| (23) | 6.00 | s |
| (22) | 6.82 | d (J = 8 Hz) |
| (19) | 6.99 | d (J = 8 Hz) |
| (20) | 7.11 | s |
| (18) | 7.03 | d (J = 16.4 Hz) |
| (17) | 7.10 | d (J = 16.4 Hz) |
| (1) | 7.46 | d (2 Hz) |
| (3) | 7.46 | d (J = 8 Hz, 2 Hz) |
| (4) | 7.64 | d (J = 8 Hz) |
| (14) | 2.00 | m |
| (15) | 0.70 | m |
| (16) | 0.70 | m |

When used as sensitizers for photopolymerizable compositions, such compositions preferably are photopolymerizable upon absorption of light in the wavelength range from 300 to 450 nm and comprise a binder, a polymerizable compound, a photoinitiator and a sensitizer, wherein the sensitizer is a divinyl fluorene compound of the present invention. The known photopolymerization initiators can be used in combination with the divinylfluorene compounds of the present invention. Suitable classes of photopolymerization initiators include aromatic ketones, aromatic onium salts, organic peroxides, thio compounds, hexaarylbisimidazole compounds, ketooxime ester compounds, borate compounds, azinium compounds, metallocene compounds, active ester compounds and compounds having a carbon-halogen bond. Many specific examples of such photoinitiators can be found in EP-A 1091247.

Good results, in particular high sensitivity, can be obtained by the combination of a divinyl fluorene sensitizer according to the present invention and a hexaarylbisimidazole (HABI, dimer of triaryl-imidazole) as photoinitiator.

A procedure for the preparation of HABIs is described in DE 1470 154 and their use in photopolymerizable compositions is documented in EP 24 629, EP 107 792, U.S. Pat. No. 4,410,621, EP 215 453 and DE 3 211 312. Preferred derivatives are e.g. 2,4,5,2',4',5'-hexaphenyl-bisimidazole, 2,2'-bis(2-chlorophenyl)-4,5,4',5'-tetraphenylbisimidazole, 2,2'-bis(2-bromophenyl)-4,5,4',5'-tetraphenylbisimidazole, 2,2'-bis(2,4-dichlorophenyl)-4,5,4',5'-tetraphenylbisimidazole, 2,2'-bis(2-chlorophenyl)-4,5,4',5'-tetrakis(3-methoxy-phenyl) bisimidazole, 2,2'-bis(2-chlorophenyl)-4,5,4',5'-tetrakis(3,4, 5-trimethoxyphenyl)-bisimidazole, 2,5,2',5'-tetrakis(2-chlorophenyl)-4,4'-bis(3,4-dimethoxyphenyl)bisimidazole, 2,2'-bis(2,6-dichlorophenyl)-4,5,4',5'-tetraphenylbisimidazole, 2,2'-bis(2-nitrophenyl)-4,5,4',5'-tetraphenylbisimidazole, 2,2'-di-o-tolyl-4,5,4',5'-tetraphenylbisimidazole, 2,2'-bis(2-ethoxyphenyl)-4,5,4',5'-tetraphenylbisimidazole and 2,2'-bis(2,6-difluorophenyl)-4,5,4',5'-tetraphenylbisimidazole. The amount of the HABI photoinitiator typically ranges from 0.01 to 30% by weight, preferably from 0.5 to 20% by weight, relative to the total weight of the non volatile components of the photopolymerizable composition.

The binder can be selected from a wide series of organic polymers. Compositions of different binders can also be used. Useful binders include for example chlorinated polyalkylenes in particular chlorinated polyethylene and chlorinated polypropylene; poly(methacrylic acid) alkyl esters or alkenyl esters in particular poly(methyl(meth)acrylate), poly(ethyl (meth)acrylate), poly(butyl(meth)acrylate), poly(isobutyl (meth)acrylate), poly(hexyl(meth)acrylate), poly((2-ethyl-hexyl)(meth)acrylate) and poly(alkyl(meth)acrylate); copolymers of (meth)acrylic acid alkyl esters or alkenyl esters with other copolymerizable monomers, in particular with (meth)acrylonitrile, vinyl chloride, vinylidene chloride, styrene and/or butadiene; poly(vinyl chloride) (PVC); vinyl-chloride/(meth)acrylonitrile copolymers; poly(vinylidene chloride) (PVDC); vinylidene chloride/(meth)acrylonitrile copolymers; poly(vinyl acetate); poly(vinyl alcohol); poly (meth)acrylonitrile; (meth)acrylonitrile/styrene copolymers; (meth)acrylamide/alkyl (meth)acrylate copolymers; (meth) acrylonitrile/butadiene/styrene (ABS) terpolymers; polystyrene; poly(α-methylstyrene); polyamides; polyurethanes; polyesters; cellulose or cellulose compounds like methyl cellulose, ethyl cellulose, acetyl cellulose, hydroxy-(C$_{1-4}$-alkyl) cellulose, carboxymethyl cellulose; poly(vinyl formal) and poly(vinyl butyral). Particularly suitable are binders that are insoluble in water, but on the other hand are soluble or at least swellable in aqueous-alkaline solutions. Further effective binders are polymers that are soluble in common organic coating solvents.

Particular suitable for the purpose of the present invention are binders containing carboxyl groups, in particular polymers or copolymers containing monomeric units of α,β-unsaturated carboxylic acids and/or monomeric units of α,β-unsaturated dicarboxylic acids, preferably acrylic acid, methacrylic acid, crotonic acid, vinylacetic acid, maleic acid or itaconic acid. By the term "copolymers" are to be understood in the context of the present invention polymers containing units of at least 2 different monomers, thus also terpolymers and higher mixed polymers. Particular useful examples of copolymers are those containing units of (meth)acrylic acid and units of alkyl(meth)acrylates, allyl(meth)acrylates and/or (meth)acrylonitrile as well as copolymers containing units of crotonic acid and units of alkyl(meth)acrylates and/or (meth)acrylonitrile and vinylacetic acid/alkyl(meth)acrylate copolymers. Also suitable are copolymers containing units of maleic anhydride or maleic acid monoalkyl esters. Among those are, for example, copolymers containing units of maleic anhydride and styrene, unsaturated ethers or esters or unsaturated aliphatic hydrocarbons and the esterification products obtained from such copolymers. Further suitable binders are products obtainable from the conversion of hydroxyl-containing polymers with intramolecular dicarboxylic anhydrides. Further useful binders are polymers in which groups with acid hydrogen atoms are present, some or all of which are converted with activated isocyanates. Examples of these polymers are products obtained by conversion of hydroxyl-containing polymers with aliphatic or aromatic sulfonyl isocyanates or phosphinic acid isocyanates. Also suitable are polymers with aliphatic or aromatic hydroxyl groups, for example copolymers containing units of hydroxyalkyl(meth)acrylates, allyl alcohol, hydroxystyrene or vinyl alcohol, as well as epoxy resins, provided they carry a sufficient number of free OH groups.

The organic polymers used as binders have a typical mean molecular weight $M_w$ between 600 and 200 000, preferably between 1 000 and 100 000. Preference is further given to polymers having an acid number between 10 to 250, preferably 20 to 200, or a hydroxyl number between 50 and 750, preferably between 100 and 500. The amount of binder(s) generally ranges from 10 to 90% by weight, preferably 20 to 80% by weight, relative to the total weight of the non-volatile components of the composition.

The polymerizable compound can be selected from a wide series of photo-oxidizable compounds. Suitable compounds contain primary, secondary and in particular tertiary amino groups. Radically polymerizable compounds containing at least one urethane and/or urea group and/or a tertiary amino group are particularly preferred. By the term "urea group" has to be understood in the context of the present invention a group of the formula >N—CO—N<, wherein the valences on the nitrogen atoms are saturated by hydrogen atoms and hydrocarbon radicals (with the proviso that not more than one valence on either of the two nitrogen atoms is saturated by one hydrogen atom). However, it is also possible for one valence on one nitrogen atom to be bonded to a carbamoyl (—CO—NH—) group, producing a biuret structure.

Also suitable are compounds containing a photo-oxidizable amino, urea or thio group, which may be also be a constituent of a heterocyclic ring. Compounds containing photo-oxidizable enol groups can also be used. Specific examples of photo-oxidizable groups are triethanolamino, triphenylamino, thiourea, imidazole, oxazole, thiazole, acetylacetonyl, N-phenylglycine and ascorbic acid groups. Particularly suitable compounds are monomers containing photo-oxidizable groups corresponding to the following formula (XVIII):

$$R_{(m-n)}Q[(-CH_2-CR^1R^2-O)_a-CO-NH-(X^1-NH-CO-O)_b-X^2-(O-CO-CR^3=CH_2)_c]_n \quad (XVIII)$$

wherein
R represents an alkyl group having 2 to 8 carbon atoms ($(C_2-C_8)$ alkyl group), a $(C_2-C_8)$ hydroxyalkyl group or a $(C_6-C_{14})$ aryl group,
Q represents —S—,

wherein
E represents a divalent saturated hydrocarbon group of 2 to 12 carbon atoms, a divalent 5- to 7-membered, saturated iso- or heterocyclic group, which may contain up to 2 nitrogen, oxygen and/or sulfur atoms in the ring, a divalent aromatic mono- or bicyclic isocyclic group of 6 to 12 carbon atoms or a divalent 5- or 6-membered aromatic heterocyclic group; and
$D^1$ and $D^2$ independently represent a saturated hydrocarbon group of 1 to 5 carbon atoms,
$R^1$ and $R^2$ independently represent a hydrogen atom, an alkyl or alkoxyalkyl group,
$R^3$ represents a hydrogen atom, a methyl or ethyl group,
$X^1$ represents a straight-chained or branched saturated hydrocarbon group of 1 to 12 carbon atoms,
$X^2$ represents a (c+1)-valent hydrocarbon group in which up to 5 methylene groups may have been replaced by oxygen atoms,
a is an integer from 0 to 4,
b is 0 or 1,
c is an integer from 1 to 3,
m is an integer from 2 to 4 and
n is an integer from 1 to m.

Compounds of this nature and processes for their preparation are described in EP 287 818. If a compound of general formula (XVIII) contains several radicals R or several radicals according to the structure indicated between square brackets, i.e. if (n–m)>1 and n>1, these radicals can be identical or different from one another. Compounds according to formula (XVIII) wherein n=m are particularly preferred. In this case, all radicals contain polymerizable groups. Preferably, the index a is 1; if several radicals are present, a cannot be 0 in more than one radical. If R is an alkyl or hydroxyalkyl group, R generally contains 2 to 6, particularly 2 to 4 carbon atoms. Aryl radicals R are in general mononuclear or binuclear, preferably however mononuclear, and may be substituted with $(C_1-C_5)$ alkyl or $(C_1-C_5)$ alkoxy groups. If $R^1$ and $R^2$ are alkyl or alkoxy groups, they preferably contain 1 to 5 carbon atoms. $R^3$ is preferably a hydrogen atom or a methyl group. $X^1$ is preferably a straight-chained or branched aliphatic and/or cycloaliphatic radical of preferably 4 to 10 carbon atoms. In a preferred embodiment, $X^2$ contains 2 to 15 carbon atoms and is in particular a saturated, straight-chained or branched aliphatic and/or cycloaliphatic radical containing this amount of carbon atoms. Up to 5 methylene groups in these radicals may have been replaced by oxygen atoms; in the case of $X^2$ being composed of pure carbon chains, the radical generally has 2 to 12 carbon atoms, preferably 2 to 6 carbon atoms. $X^2$ can also be a cycloaliphatic group of 5 to 10 carbon atoms, in particular a cyclohexane diyl group. The saturated heterocyclic ring formed by $D^1$, $D^2$ and both nitrogen atoms generally has 5 to 10 ring members in particular 6 ring members. In the latter case the heterocyclic ring is preferably a piperazine and the radical derived therefrom a piperazine-1,4-diyl radical. In a preferred embodiment, radical E is an alkane diyl group which normally contains about 2 to 6 carbon atoms. Preferably the divalent 5- to 7-membered, saturated, isocyclic group E is a cyclohexane diyl group, in particular a cyclohexane-1,4-diyl group. The divalent, isocyclic, aromatic group E is preferably an ortho-, meta- or para-phenylene group. The divalent 5- or 6-membered aromatic heterocyclic group E, finally, contains preferably nitrogen and/or sulphur atoms in the heterocyclic ring. c is preferably 1, i.e. each radical in the square bracket generally contains only one polymerizable group, in particular only one (meth) acryloyloxy-group.

The compounds of formula (XVIII) wherein b=1, which accordingly contain two urethane groups in each of the radicals indicated in the square brackets, can be produced in a known way by conversion of acrylic esters or alkacrylic esters which contain free hydroxyl groups with equimolar amounts of diisocyanates. Excess isocyanate groups are then, for example, reacted with tris(hydroxyalkyl)amines, N,N'-bis(hydroxyalkyl)piperazines or N,N,N',N'-tetrakis(hydroxyalkyl)alkylenediamines, in each of which individual hydroxyalkyl groups may have been replaced by alkyl or aryl groups R. If a=0, the result is a urea grouping. Examples of the hydroxy-alkylamine starting materials are diethanolamine, triethanolamine, tris(2-hydroxypropyl)amine, tris(2-hydroxybutyl)amine and alkyl-bis-hydroxyalkylamines. Examples of suitable diisocyanates are hexamethylene diisocyanate, 2,2,4-trimethylhexamethylene diisocyanate, 1,4-cyclohexylene diisocyanate (=1,4-diisocyanatocyclohexane) and 1,1,3-trimethyl-3-isocyanatomethyl-5-isocyanatocyclohexane. The hydroxy-containing esters used are preferably hydroxyethyl(meth)acrylate, hydroxypropyl(meth)acrylate and hydroxyisopropyl(meth)acrylate.

The polymerizable compounds of formula (XVIII) wherein b=0 are prepared converting the above-described hydroxyalkylamino compounds with isocyanate-containing acrylic or alkacrylic esters. A preferred isocyanate-containing ester is isocyanoto-ethyl (meth)acrylate.

Further polymerizable compounds comprising photooxidisable groups suitable for the purpose of the invention are compounds according to the following formula (XIX):

$$R_{(m-n)}Q[(-CH_2-CR^1R^2-O)_{a'}-(CH_2-CH[CH_2-O-CO-CR^3=CH_2]-O)_{b'}-H]_n \quad (XIX)$$

wherein a' and b' independently represent integers from 1 to 4 and Q, $R^1$, $R^2$, $R^3$, n and m have the same meaning as above and Q can also be a group of the formula >N—E'—N< wherein the radical E' corresponds to the following formula (XX):

$$-CH_2-CH(OH)-CH_2-[O-(p)C_6H_4-C(CH_3)_2-(p)C_6H_4-CH_2-CH(OH)-CH_2-]_c \quad (XX)$$

wherein c has the same meaning as in formula (II) and $(p)C_6H_4$ represents para-phenylene.

The compounds of formula (XIX) are prepared analogously to those of formula (XVIII), except that the conversion products of hydroxyalkyl acrylates or alkacrylates and diisocyanates are replaced by the corresponding acrylic and alkacrylic glycide esters. Compounds of formula (XX) and processes to their preparation are disclosed in EP 316 706.

Further useful polymerizable compounds containing photooxidisable groups are acrylic and alkacrylic esters of the following formula (XXI):

$$Q'[(-X^{1'}-CH_2-O)_a-CO-NH(-X^1-NH-CO-O)_b-X^2-O-CO-CR^3=CH_2]_n \quad (XXI)$$

wherein

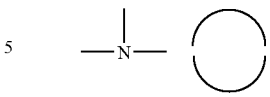

Q' represents

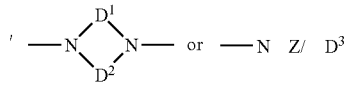

wherein $D^1$ and $D^2$ independently represent a saturated hydrocarbon group of 1 to 5 carbon atoms and $D^3$ represents a saturated hydrocarbon group of 4 to 8 carbon atoms, which together with the nitrogen atom forms a 5- or 6-membered heterocyclic ring;

$X^{1'}$ represents $-C_iH_{2i}-$ or

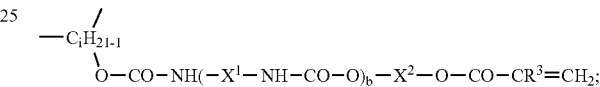

Z represents a hydrogen atom or a radical of the following formula:

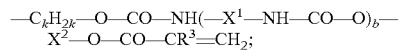

i,k independently represent integers from 1 to 12;

n' represents an integer from 1 to 3; and a is 0 or 1; provided that a is 0 in at least one of the radicals bonded to Q;

$X^1$, $R^3$, a and b have the same meaning as given in the above formula (VIII); and $X^2$ represents a divalent hydrocarbon group in which up to 5 methylene groups may be replaced by oxygen atoms.

In formula (XXI) index a is preferably 0 or 1 and i preferably represents a number between 2 and 10. Preferred radicals Q are piperazine-1,4-diyl ($D^1=D^2=CH_2-CR_2$), piperidine-1-yl ($D^3=(CH_2)_5$, Z=H) and 2-(2-hydroxyethyl)-piperidine-1-yl ($D^3=(CH_2)_5$, Z=$CH_2CH_2OH$).

Of the compounds of formula (XXI), those which apart from a urea group contain at least one urethane group are preferred. Here again, by the term "urea group" has to be understood the group of formula >N—CO—N< already mentioned above. Compounds of formula (XXI) and processes for their preparation are disclosed in EP 355 387.

Also suitable polymerizable compounds are reaction products of mono- or diisocyanates with multifunctional alcohols, in which the hydroxy groups are partly or completely esterified with (meth)acrylic acid. Preferred compounds are materials, which are synthesized by the reaction of hydroxyalkyl-(meth)acrylates with diisocyanates. Such compounds are basically known and for instance described in DE 28 22 190 and DE 20 64 079.

The amount of polymerizable compound comprising photooxidisable groups generally ranges from 5 to 75% by weight, preferably from 10 to 65% by weight, relative to the total weight of the non volatile compounds of the photopolymerizable composition.

Moreover, the composition can contain polyfunctional (meth)acrylate or alkyl(meth)acrylate compounds as crosslinking agents. Such compounds contain more than 2, preferably between 3 and 6 (meth)acrylate and/or alkyl(meth) acrylate groups and include in particular (meth)acrylates of saturated aliphatic or alicyclic trivalent or polyvalent alcohols such as trimethylol ethane, trimethylol propane, pentaerythritol or dipentaerythritol.

The total amount of polymerizable compounds generally ranges from about 10 to 90% by weight, preferably from about 20 to 80% by weight, relative to the total weight of the non volatile components of the photopolymerizable composition comprising the divinylfluorene compound of the present invention.

The following specific example is also a suitable polymerizable compound:

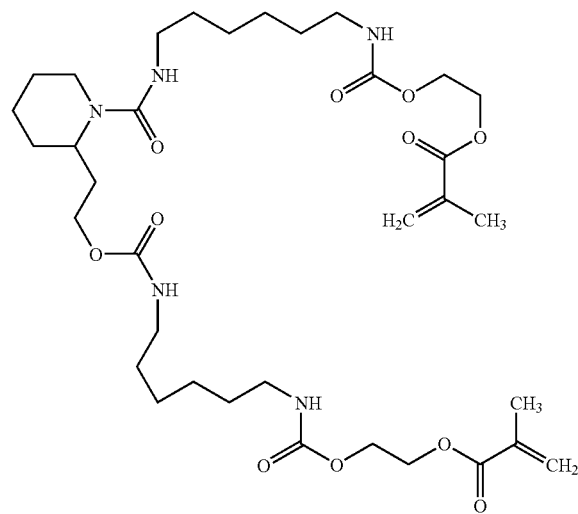

In order to achieve a high sensitivity, it is advantageous to add a radical chain transfer agent as described in EP 107 792 to the photopolymerizable composition in combination with the divinylfluorene compound of the present invention. The preferred chain transfer agents are sulfur containing compounds, especially thiols like e.g. 2-mercaptobenzothiazole, 2-mercaptobenzoxazole or 2-mercapto-benzimidazole. The amount of chain transfer agent generally ranges from 0.01 to 10% by weight, preferably from 0.1 to 2% by weight, relative to the total weight of the non volatile components of the photopolymerizable composition.

In order to adjust the photopolymerizable composition comprising the divinyl compound according to the present invention to specific needs, thermal inhibitors or stabilizers for preventing thermal polymerization may be added. Furthermore additional hydrogen donors, dyes, colored or colorless pigments, color formers, indicators and plasticisers may be present. These additives are conveniently selected so that they absorb as little as possible in the actinic range of the imagewise applied radiation.

The photopolymerizable composition comprising the divinyl fluorene according to the present invention is applied to the support by processes which are known per se to the person skilled in the art. In general, the components of the photopolymerizable composition are dissolved or dispersed in an organic solvent or solvent mixture, the solution or dispersion is applied to the intended support by pouring on, spraying on, emersion, roll application or in a similar way, and the solvents are removed during the subsequent drying.

The known supports can be used for the photopolymer printing plate comprising the divinyl fluorene compounds of the present invention, like e.g. foils, tapes or plates made of metal or plastics and in the case of screen-printing also of Perlon gauze. Preferred metals are aluminium, aluminium alloys, steel and zinc, aluminium and aluminium alloys being particularly preferred. Preferred plastics are polyester and cellulose acetates, poly-ethyleneterephthalate (PET) being particularly preferred.

In most cases it is preferred, to treat the surface of the support mechanically and/or chemically and/or electro-chemically to optimally adjust the adherence between the support and the photosensitive coating and/or to reduce the reflection of the imagewise exposed radiation on the surface of the support (antihalation).

The most preferred support to be used for the photopolymer printing plates is made of aluminium or an aluminium alloy, its surface is electrochemically roughened, thereafter anodized and optionally treated with a hydrophilizing agent like e.g. poly(vinylphosphonic acid).

Such printing plate precursors preferably have a protective layer (overcoat layer) provided on top of the photopolymerizable layer.

Said protective layer may contain the ingredients known in the art, in particular water soluble polymers like poly(vinyl alcohols) or poly(vinyl pyrrolidone), surface wetting agents, coloring agents, complexants and biocides. Among said complexants, ethoxylated ethylene diamine compounds have been found to be particularly preferred in combination with the divinyl fluorene compounds of the present invention.

Preferably the protective overcoat comprises at least one type of poly(vinyl alcohol), wherein the mean degree of saponification is less than 93 mol-%.

The degree of saponification is related to the production of poly(vinyl alcohols). As the monomer of poly(vinyl alcohol), vinyl alcohol, is nonexistent, only indirect methods are available for the production of poly(vinyl alcohol). The most important manufacturing process for poly(vinyl alcohol) is the polymerization of vinyl esters or ethers, with subsequent saponification or transesterification. The preferred starting material for the poly(vinyl alcohol) used in the context of the present invention is a vinyl alcohol esterified by a mono carboxylic acid and in particular vinyl acetate, but derivatives of vinyl acetate, vinyl esters of di carboxylic acids, vinyl ethers and the like can also be used. The degree of saponification as defined in the context of the present invention is the molar degree of hydrolysis irrespective of the process used for the hydrolysis. Pure poly(vinyl alcohol) has e.g. a degree of saponification of 100 mol-%, but commercial products often have a degree of saponification of 98 mol-%. The poly(vinyl alcohols) as preferably used in the context of the present invention contain mainly 1,3-diol units, but may also contain small amounts of 1,2-diol units. In the partially saponified poly(vinyl alcohols) the ester or the ether group can be distributed statistically or block-wise. Preferred partially saponified poly(vinyl alcohols) used in the context of the present invention have a viscosity of a 4% aqueous solution at 20° C. of 4 to 60 mPa·s, preferably of 4 to 20 mPa·s and in particular of 4 to 10 mPa·s.

Poly(vinyl alcohols) preferred in the context of the present invention are commercially available e.g. under the tradename Mowiol. Those products are characterised by two appended numbers, meaning the viscosity and the degree of saponification. For example, Mowiol 8-88 or Mowiol 8/88 mean a poly(vinyl alcohol) having as 4% aqueous solution at 20° C. a viscosity of ca 8 mPa·s and a degree of saponification of 88 mol-%. It is further preferred to use a mixture of two or more compounds. Preferably poly(vinyl alcohols) differing in viscosity as defined above and/or in saponification degree are combined. Particularly preferred are mixture of poly(vinyl alcohols) that differ in viscosity of their 4% aqueous solutions at 20° C. for at least 2 mPa·s or that differ in saponification degree for at least 5 mol-%. Most preferred are mixtures comprising at least 3 types of poly(vinyl alcohols), wherein at least two compounds differ in viscosity as defined above for at least 2 mPa·s and at least two compounds differ in saponification degree for at least 5 mol-%.

Preferably the overall mean saponification degree of all poly(vinyl alcohols) used in the protective layer has to be less than 93 mol-%. In the context of the present invention it is further preferred, that said overall mean saponification degree ranges from 71 mol-% to less than 93 mol-% and in particular from 80 mol-% to 92.9 mol-%.

The overall mean saponification degree of the poly(vinyl alcohols) used in the protective overcoat of a printing plate precursor can be determined experimentally via $^{13}$C-NMR. To measure the $^{13}$C-NMR spectra, approximately 200 mg of the protective overcoat are dissolved in 1.0 ml DMSO and from this solution a 75 MHz $^{13}$C-NMR spectrum is taken, whose resonances can easily be interpreted and allow to calculate the degree of saponification (experimental values). A good correlation is obtained between said experimental values and the values known from the product specification of the poly(vinyl alcohols). The latter values are hereinafter called theoretical values of the mean saponification degree and can easily be calculated, when mixture of poly(vinyl alcohols) are used.

Preferably the poly(vinyl alcohol) is used in 50 to 99.9 weight percent (wt. %) relative to the total weight of the non-volatile compounds of the protective overcoat. Additionally other water soluble polymers can be added to the layer such as poly(vinyl pyrrolidone), poly(ethylene oxide), gelatin, gum arabic, oxygen binding polymers with aliphatic amine groups known from EP 352 630 B1, methyl vinylether/maleic anhydride copolymers, poly(carboxylic acids), copolymers of ethylene oxide and poly(vinyl alcohol), carbon hydrates, hydroxy ethyl cellulose, acidic cellulose, cellulose, poly(arylic acid) and mixtures of these polymers.

Preferably the poly(vinyl pyrrolidone) is only used in small quantities compared to the poly(vinyl alcohol), in particular poly(vinyl pyrrolidone) is used from 0 to 10 parts by weight of the poly(vinyl alcohol) used, from 0 to 3 parts by weight being particularly preferred. Most preferred no poly(vinyl pyrrolidone)compounds are used.

In addition to the poly(vinyl alcohol) and the optional water-soluble polymers disclosed above, the known ingredients of protective layers can be used.

The protective layer has to be transparent for actinic light and preferably has a dry thickness of 0.2 to 10 g/m², 1.0 to 5 g/m² being particularly preferred. Preferably it is homogeneous, substantially impermeable to oxygen, waterpermeable, and can be washed off preferably with the conventional developer solutions used to form a printing relief after image-wise exposure of the photosensitive layer. Said photopolymerizable layer is removed imagewise, whereas the protective layer is removable over the entire area of the element created. The wash-off of the protective layer can be done in a separate step, but can be done during the development step as well.

The protective layer can be coated on the photosensitive layer with known techniques and the coating solution preferably contains water or a mixture of water and an organic solvent. To allow a better wetting, the coating solution preferably contains, related to the solid content, up to 10 wt. %, and particular preferred up to 5 wt. % of a surface active agent. Suitable representatives of surface active agents comprise anionic, cationic and nonionic surface active agents like sodium alkylsulfates and -sulfonates having 12 to 18 carbon atoms, an example of which is sodium dodecylsulfate, N-cetyl- and C-cetyl betaine, alkylaminocarboxylate and -dicarboxylate, and polyethylene glycols with a mean molar weight up to 400.

In addition, further functions can be added to the protective layer. For example, it can be possible to improve the safelight suitability without decreasing the sensitivity of the layer by adding a coloring agent, e.g. a water-soluble dye, that has excellent transmission to the light having a wavelength of 300 to 450 nm and that absorbs the light having a wavelength of 500 nm or more. This principle can easily be varied for different wavelengths to adjust the effective spectral sensitivity distribution of the printing plate precursor as needed.

The photopolymerizable composition comprising the divinylfluorene compound of the present invention can also be used in a method of making a lithographic printing plate comprising the steps of providing a photopolymer printing plate precursor comprising said composition, exposing said printing plate precursor with light comprising radiation in the wavelength range from 300 to 450 nm, preferably with a laser having an emission wavelength in the range from 300 to 450 nm, and processing the printing plate precursor in an aqueous alkaline developer.

In such a process the exposure is done with light comprising radiation in the wavelength range from 350 to 430 nm, preferably from 380 to 430 nm, in particular from 390 to 420 nm and preferably the exposure is done with a laser having an emission wavelenth in the range from 350 to 430 nm, preferably from 380 to 430 nm, in particular in the range from 390 to 420 nm, and the exposure is carried out at an energy density, measured on the surface of the plate, of 100 µJ/cm² or less and preferably of 80 µJ/cm² or less.

The processing of the printing plate precursor comprising the divinylfluorene compound of the present invention is done in the usual manner. After image-wise exposure a pre-heat step is performed to improve the crosslinking of the photosensitive layer. Usually the pre-heat step is then followed by the development step, wherein the complete overcoat layer and the unexposed part of the photosensitive layer are removed. The removal (wash-off) of the overcoat layer and the development of the photosensitive layer can be done in two separate steps in this order, but can also be done in one step simultaneously. Preferably the overcoat layer is washed-off with water before the development step. What remains on the support after the development step are the exposed and thereby photopolymerized parts of the photosensitive layer. The developer solution used for the development of the exposed printing plate precursors preferably is an aqueous alkaline solution having a pH of at least 11, a pH from 11.5 to 13.5 being particularly preferred. The developer solution can contain a small percentage, preferably less than 5 wt. %, of an organic, water-miscible solvent. To adjust the pH of the solution, an alkali hydroxide is preferably used.

Examples of preferred, additional ingredients of the developer solution comprise alone or in combination alkali phosphates, alkali carbonates, alkali bicarbonates, an organic amine compound, alkali silicates, buffering agents, complexants, defoamers, surface active agents and dyes, but the suitable ingredients are not limited to the preferred examples and further ingredients can be used.

The method of development employed is not particularly limited, and may be conducted by soaking and shaking the plate in a developer, physically removing non-image portions while being dissolved in a developer by means of e.g. a brush, or spraying a developer onto the plate so as to remove non-image portions. The time for development is selected depending upon the above method used so that the non-image portions can adequately by removed, and is optionally selected within a range of 5 seconds to 10 minutes.

After the development, the plate my be subjected to a hydrophilic treatment by means of, e.g., gum arabic optionally applied to the printing plate as the case requires (gumming step).

The divinylfluorene compounds of the present invention are stable compounds that usually absorb strongly in the long UV range at about 380 to 390 nm and emit blue fluorescence with a high quantum yield and therefore are good optical brighteners.

In particular those compounds of formulae (II) and (III) that comprise polymerizable substituents, e.g. comprising double or triple bonds or phenolic functions, can be polymerized or copolymerized by known synthetic methods, such as those disclosed in US2003/0091859 to light emitting materials of electroluminescent elements like those disclosed in GB 2 313 127 under formula (I) and US2003/0091859. Therefore the compounds of formulae (II) and (III) of the present invention make possible a new synthetic route to such light emitting materials and also provides access to new polymeric light emitting materials.

EXAMPLES

A. Preparation (Coating) of the Photosensitive Layer

A composition was prepared (pw=parts per weight; wt. %=weight percentage) by mixing the components as specified in table 4. This composition was divided equally into 10 portions, and to each portion was added an amount of sensitizer according to table 5. The resulting composition was coated on an electrochemically roughened and anodically oxidized aluminum sheet, the surface of which has been rendered hydrophilic by treatment with an aqueous solution of polyvinyl phosphonic acid (oxide weight 3 g/m$^2$) and was dried for 1 minute at 120° C. (circulation oven). The resulting thickness of the layer was 1.5 g/m$^2$.

TABLE 4

| Component | Parts per weight (g) |
|---|---|
| a solution containing 32.4 wt. % of a methacrylate/methacrylic acid copolymer (ratio methylmethacrylate:methacrylic acid of 4:1 by weight; acid number: 110 mg KOH/g) in 2-butanone (viscosity 105 mm$^2$/s at 25° C.). | 16.075 |
| a solution containing 88.2 wt. % of a reaction product from 1 mole of 2,2,4-trimethyl-hexa-methylenediisocyanate and 2 moles of hydroxyethyl-methacrylate (viscosity 3.30 mm$^2$/s at 25° C.) | 14.538 |
| Heliogene blue D 7490 ® dispersion (9.9 wt. %, viscosity 7.0 mm$^2$/s at 25° C.), trade name of BASF AG | 17.900 |
| 2,2'-bis(2-chlorophenyl)-4,4',5,5'-tetraphenyl-1,2-bisimidazole | 1.448 |
| 2-mercaptobenzothiazole | 0.068 |
| Edaplan LA 411 ® (1% in Dowanol PM ®, trade mark of Dow Chemical Company) | 2.250 |
| 2-butanone | 78.538 |
| propyleneglycol-monomethylether (Dowanol PM ®, trade mark of Dow Chemical Company) | 130.358 |

TABLE 5

| Experiment | Sensitizer | Amount of sensitizer (mmol) |
|---|---|---|
| A | 1,4-di(3,4,5-trimethoxy-styryl)benzene | 0.175 |
| B | 1,4-di[3,5-dimethoxy-4-(1-methylpropoxy)styryl]benzene | 0.175 |
| C | 4,4'-di[3,5-dimethoxy-4-(1-methylpropoxy)styryl]biphenyl | 0.175 |
| D | 1,4-di[3,5-dimethoxy-4-(1-methylpropoxy)styryl]-2,3,5,6-tetrachlorobenzene | 0.175 |
| E | (II-1) | 0.175 |
| F | (II-2) | 0.175 |
| G | (II-5) | 0.175 |

On top of the photosensitive layer a solution in water with the composition as defined in table 6 was coated and was dried at 110° C. for 2 minutes.

TABLE 6

| Component | Parts by Weight (g) |
|---|---|
| partially hydrolyzed polyvinylalcohol (degree of hydrolysis 88%, viscosity 4 mPa · s in a solution of 4 wt. % at 20° C.). | 17.03 |
| partially hydrolyzed polyvinylalcohol (degree of hydrolysis 88%, viscosity 8 mPa · s in a solution of 4 wt. % at 20° C.). | 7.43 |
| fully hydrolyzed polyvinylalcohol (degree of hydrolysis 98%, viscosity 6 mPa · s in a solution of 4 wt. % at 20° C.). | 14.87 |
| CA 24 E | 0.26 |
| Metolat FC 355 | 0.38 |
| Lutensol A8 (90%) | 0.032 |
| Water | 960 |

The so formed protective overcoat had a dry thickness of 2.0 g/m$^2$.

The imaging was carried out with a Polaris XsV violet platesetter device (flat bed system) equipped with a violet laser diode emitting between 392 and 417 nm. The following imaging conditions were used:

Scanning speed: 1000 m/sec

Variable image plane power: 0 to 10.5 mW

Spot diameter: 20 μm

Addressability: 1270 dpi

After imaging the plate was processed in a Agfa VSP85s processor at a speed of 1.2 m/min. During the processing the plate was first heated to 110° C. (pre-heat step), next the protective overcoat was washed off and the photolayer was processed in a water based alkaline developer (Agfa PD91) at 28° C. After a water rinsing and gumming step the printing plate was ready. A 13-step exposure wedge with density increments of 0.15 was used to determine sensitivity of the plate. The results of the exposure tests are shown in table 7 as relative values, wherein the sensitivity of the plate prepared with experiment A (material A) was arbitrarily set to 100%. For example a relative sensitivity of 200% corresponds to a material that, compared to material A, only needs 50% of the exposure energy density (μJ/cm$^2$) for a complete hardening of three wedge steps (the coating is considered as being completely hardened when the density of the processed material is at least 97% of the density of a plate which has been exposed without filter).

TABLE 7

| Experiment | Relative sensitivity (%) | |
|---|---|---|
| A | 100 | comparison |
| B | 103 | comparison |
| B(2) | 99 | comparison |
| C | 77 | comparison |
| D | No image | comparison |
| E | 128 | invention |
| E(2) | 133 | invention |
| F | 141 | invention |
| F(2) | 133 | invention |
| G | 139 | invention |

It can be clearly seen that there is a significant gain in sensitivity when distyrylfluorene-type sensitizers of the present invention are used compared to the sensitizers known from the state of the art. The experiments B, E and F were run twice as B(2), E(2) and F(2). Their results demonstrate the very good reproducibility of the data.

The invention claimed is:

1. A divinylfluorene compound according to formula (II):

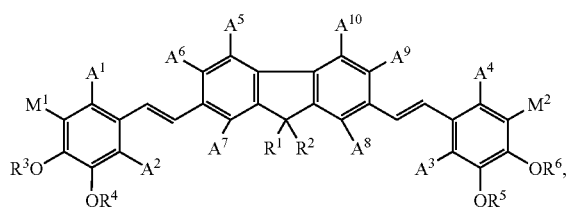

(II)

wherein $A^1$ to $A^{10}$ and $R^1$ and $R^2$ are mutually independent substituents selected from the group consisting of hydrogen, alkyl, alkenyl, alkynyl, aryl, heterocyclyl, hydroxy, carboxy, carbalkoxy, halogeno, alkoxy, aryloxy, heterocyclyloxy, alkylthio, arylthio, heterocyclylthio, alkylseleno, arylseleno, heterocyclylseleno, acyl, acyloxy, alkylsulfonyl, aminosulfonyl, acylamino, cyano, nitro, amino and mercapto groups, wherein the heterocyclyl of heterocyclyl, heterocyclyloxy, heterocyclylthio, and heterocyclylseleno is a saturated, unsaturated or aromatic heterocyclyl group and acyl is the residue of an aliphatic, olefinic or aromatic carboxylic, carbaminic, sulfonic, amidosulfonic or phosphonic acid, $M^1$ is a hydrogen atom or $OR^7$, $M^2$ is a hydrogen atom or $OR^8$, and $R^3$ to $R^8$ are mutually independent and are a hydrogen atom, alkyl, an alkyl chain containing double or triple bonds, alkenyl, alkynyl, or a non-metallic atom group linked to the oxygen by a carbon atom, wherein the non-metallic atom group is selected from the group consisting of aryl, heterocyclyl, hydroxy, carboxy, carbalkoxy, halogeno, alkoxy, aryloxy, heterocyclyloxy, alkylthio, arylthio, heterocyclylthio, alkylseleno, arylseleno, heterocyclylseleno, acyl, acyloxy, alkylsulfonyl, aminosulfonyl, acylamino, cyano, nitro, amino and mercapto groups, wherein the heterocyclyl of heterocyclyl, heterocyclyloxy, heterocyclylthio, and heterocyclylseleno is a saturated, unsaturated or aromatic heterocycle and acyl is the residue of an aliphatic, olefinic or aromatic carboxylic, carbaminic, sulfonic, amidosulfonic or phosphonic acid, and wherein one or more pairs of said substituents may jointly form a ring.

2. The divinylfluorene compound according to claim 1, wherein at least one of the substituents $R^1$ to $R^8$ is not a hydrogen atom.

3. The divinylfluorene compound according to claim 1, wherein $A^1$ to $A^{10}$ are hydrogen.

4. The divinylfluorene compound according to claim 1, wherein $R^1$ and $R^2$ are mutually independent and are a straight chain or branched alkyl having 1 to 20 carbon atoms.

5. The divinylfluorene compound according to claim 1, wherein the divinylfluorene compound is symmetrical.

6. The divinylfluorene compound according to claim 1, wherein $R^3$ to $R^8$ are mutually independent and are a substituent selected from hydrogen and alkyl.

* * * * *